United States Patent [19]
Purbrick et al.

[11] Patent Number: 4,773,970
[45] Date of Patent: Sep. 27, 1988

[54] ION-SENSITIVE ELECTROCHEMICAL SENSOR AND METHOD OF DETERMINING ION CONCENTRATIONS

[75] Inventors: Malcolm D. Purbrick, Hertfordshire; Karel L. Petrak, Middlesex; Derek A. Thomason, Hertfordshire, all of England

[73] Assignee: Eastman Kodak Company, Rochester, N.Y.

[21] Appl. No.: 902,906

[22] Filed: Sep. 2, 1986

[30] Foreign Application Priority Data

Sep. 6, 1985 [GB] United Kingdom ............... 8522207

[51] Int. Cl.⁴ .................. G01N 27/26; G01N 27/30; G01N 27/40
[52] U.S. Cl. ............................ 204/1 T; 204/418; 357/25
[58] Field of Search .............. 204/418, 1 B, 296; 357/25

[56] References Cited

U.S. PATENT DOCUMENTS

| | | | |
|---|---|---|---|
| 4,020,830 | 3/1977 | Johnson et al. | 128/2 |
| 4,221,642 | 9/1980 | De Nora et al. | 204/98 |
| 4,273,636 | 6/1981 | Shimada et al. | 204/195 |

FOREIGN PATENT DOCUMENTS

2076545 2/1984 United Kingdom.

Primary Examiner—John F. Niebling
Assistant Examiner—Steven P. Marquis
Attorney, Agent, or Firm—John R. Everett

[57] ABSTRACT

An ion-sensitive electrochemical sensor comprises an electrode body having an ion-sensitive polymeric membrane coated thereon. The membrane comprises a water-insoluble copolymer having ion exchange sites and has a glass transition temperature greater than about 80° C. The sensor is used to determine ion concentration by contacting it with a test solution and determining the ion concentration as a function of the potential of the electrode.

12 Claims, 4 Drawing Sheets

ION-SENSITIVE ELECTROCHEMICAL SENSOR AND METHOD OF DETERMINING ION CONCENTRATIONS

FIELD OF THE INVENTION

This invention relates to ion-sensitive electrochemical sensors and to methods of determining ion concentrations therewith. More particularly, the invention relates to electrochemical sensors comprising a solid-state electrode body having an ionsensitive polymeric membrane coated thereon.

BACKGROUND OF THE INVENTION

Electrochemical sensors comprising a selfsupporting ion-sensitive polymeric membrane are well known in the art. In use, such membranes separate a solution being tested from an internal reference solution. Such sensors have membranes that are self-supporting, which need not be coated on a solid-state electrode body. For example, U.K. Pat. No. 2,076,545 describes such a sensor in which the membrane comprises a copolymer having ion-exchange sites with the copolymer having a glass transition temperature ($T_g$) less than 20° C. Such a copolymer is very difficult to prepare, often resulting in a non-functioning sensor.

Electrochemical sensors comprising a solid-state electrode body having an ion-sensitive polymeric membrane coated on a surface thereof are also well known. For example, U.S. Pat. No. 4,020,830 describes a chemical sensitive field effect transistor transducer capable of selectively detecting and measuring chemical properties of substances to which the transducer is exposed. The transducer includes a semiconductor substrate material having a certain doping polarity, a pair of spaced apart diffusion regions located at the surface of the substrate material and having a doping polarity opposite to that of the substrate material, electrical insulating material overlying the diffusion regions and the surface of the substrate material lying between the diffusion regions, and a chemical selective system overlying the insulator material. The chemical selective system may be an ion-sensitive polymeric membrane such as a membrane comprising a polyvinyl chloride matrix having an ion-exchange material dispersed therein.

It is also known to use such an ion-sensitive polymeric membrane in an electrochemical sensor of the coated wire electrode type where the membrane is coated on the surface of a solid electron conductor, such as a metal wire. The membrane in such sensors allows a selective ion exchange to occur between the ion-exchange material and a solution to which the membrane is exposed. The potential difference generated electrochemically between the membrane and the solution may be used to measure the concentration of a particular ion in solution.

SUMMARY OF THE INVENTION

The present invention provides an electrochemical sensor having an alternative ion-sensitive polymeric membrane. The polymeric membrane is easily prepared, resulting in a properly functioning sensor. The polymer has favorable handling characteristics and is readily purified, which facilitates the production of a sensor having good reliability and reproducibility. Also, the ion-exchange material is not leached from the membrane when in use.

In accordance with the present invention there is provided an ion-sensitive electrochemical sensor comprising an electrode body having an ion-sensitive polymeric membrane coated thereon, wherein the membrane comprises a water-insoluble copolymer having ion-exchange sites. The copolymer has a glass transition temperature ($T_g$) greater than about 80° C. Preferably, the membrane also comprises a plasticizer.

The present invention also comprises a method of determining ion concentration in an aqueous liquid comprising contacting the test solution with the sensor described above and determining the concentrations of ions in solution as a function of the potential of the electrode.

DESCRIPTION OF THE PREFERRED EMBODIMENTS

Figure 1:
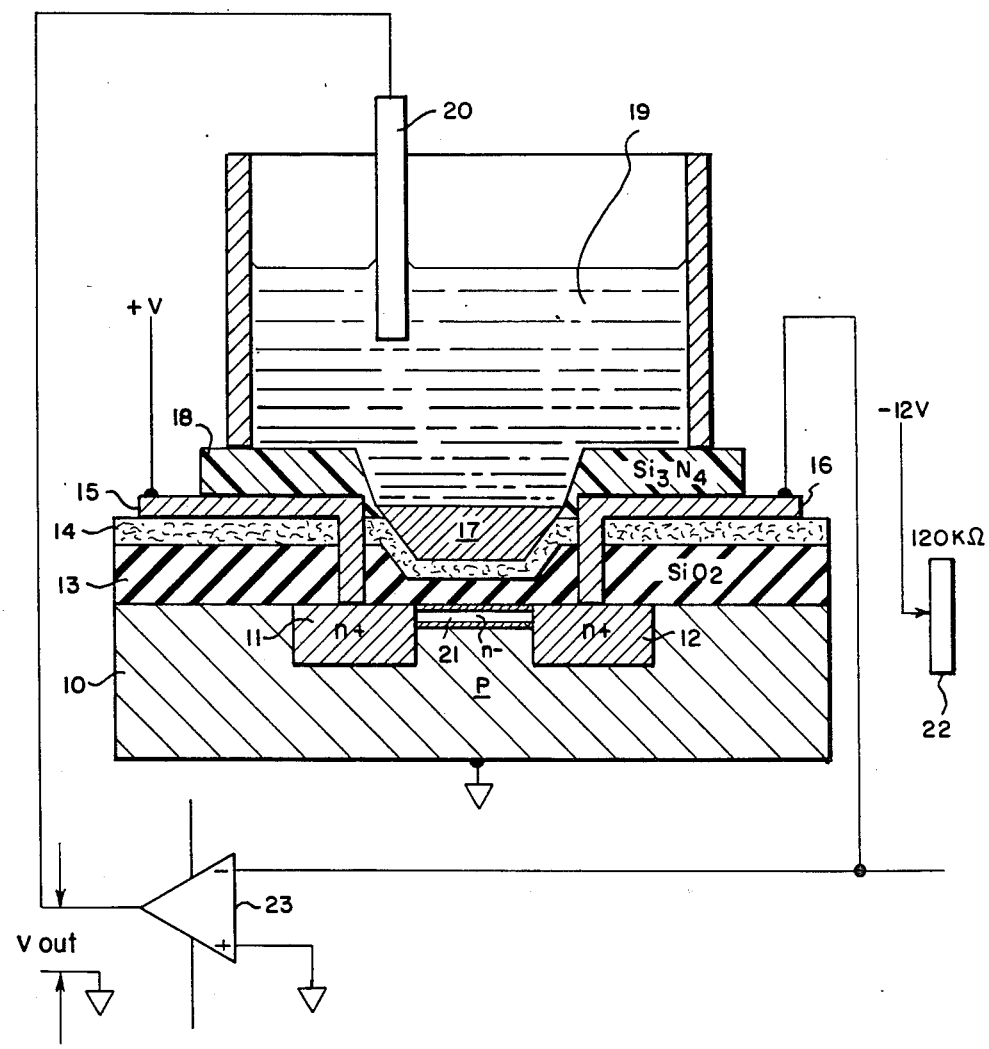
FIG. 1 is a schematic view of an ion-sensitive field effect transistor of the invention (ISFET) in use.

The copolymer of the invention contains comonomer units having ion-exchange sites, which units are referred to hereafter as ionic units. The comonomer units having ion-exchange sites preferably comprise from about 0.5% to 90% by weight of the copolymer, and more preferably from about 5% to 25% by weight. The ionic units of the copolymer may contain cationic groups such as a tertiary nitrogen quaternized with, for example, methyl iodide, ethyl chloride, methyl p-toluene sulphonate, benzyl chloride, or benzhydryl chloride. Co-monomers containing tertiary nitrogen groups can be converted later into the corresponding quaternary salt groups by reacting with a quaternizing agent including vinyl substituted nitrogen-containing heterocyclic compounds such as pyridine, imidazole, quinoline, isoquiniline, pyrimidine, phenanthroline, benzothiazole, purine, pyrazine, acridine, or picoline.

Alternatively, the ionic units of the copolymer may contain anionic groups such as an acidic group, preferably a carbocyclic or sulphonic acid group. For example, an acrylic acid, vinyl phenol or vinyl phenyl sulphonic acid, or a salt or phenolate thereof may be employed as a comonomer.

The other comonomer units of the copolymer can be derived from non-polar comonomers, which, when used in an appropriate amount, will give the copolymer a $T_g$ preferably greater than about 80° C., and more preferably greater than about 100° C. The copolymer may comprise from about 10% to 99.5% by weight, preferably about 75% to 95% by weight, of non-polar comonomer units which may be derived from one or more monomers. The comonomer may be selected from the wide range of known free radical polymerizable monomers. In order to provide the sufficiently high $T_g$, the monomer must be capable of exhibiting a good packing density when polymerized and, accordingly, will generally be a relatively simple, unsubstituted monomer. Suitable comonomers may be selected from acrylates (e.g. methyl methacrylates), olefins, styrenes, and vinyl ethers.

Crosslinkable monomers may also be employed. For example, divinyl benzene, chloromethylstyrene, or bisacrylate could be used. Crosslinking can also be achieved by reacting a copolymer containing an imidazole or similar ring with a bis-epoxy compound.

It is to be understood that any of the above variants, singly or in combination, may be employed to give the copolymer the desired physical properties.

The copolymers may be prepared by known techniques, including copolymerization of the comonomers with subsequent introduction of ionic groups as required. For example, methyl methacrylate may be copolymerized with vinyl imidazole to produce a water-insoluble copolymer. The copolymer may be quaternized with a quaternizing agent, e.g. benzylchloride, to create immobilized ion-exchange sites in the copolymer. A membrane of this copolymer would be sensitive to chloride ions. Different counter ions may be introduced by an ion-exchange reaction, as is known in the art. Thus, for example, the chloride ion in the above copolymer could be exchanged for a surfactant anion, e.g., dodecyl sulphate, to render the membrane of the copolymer sensitive to an anionic surfactant.

A preferred copolymer comprises units derived from methyl methacrylate and N-vinyl imidazole in a ratio from about 10:1 to 25:1.

In order to form a membrane of the copolymer, a plasticizer may be employed in an amount which will impart desired sensing characteristics and/or film-forming properties to the copolymer. The plasticizr is preferably present in an amount from about 5% to 70%, and more preferably from about 20% to 60% by weight based on the copolymer. Any conventional known plasticizer may be used, depending on the particular copolymer. Suitable plasticizers include phosphoric acid esters such as tricresyl phosphate, phthalic acid esters such as dipentyl phthalate, adipic acid esters and sebacic acid esters such as bis-(2-ethylhexyl) sebacate. Additional suitable plasticizers are disclosed in "Neutral Carrier based ISE's", Amman et al, ISE Reviews, 5, 1893, 3-92.

The membrane of the invention may be prepared by first forming a solution of the copolymer and, if desired, the plasticizer in a suitable solvent such as tetrahydrofuran. The solution is coated on a surface of the sensor by known techniques such as dipping or spraying, and the solvent is evaporated to form the membrane. Slow evaporation of the solvent is preferred to avoid the formation of pinholes in the membrane. Preferably, the membrane is made as thin as possible to provide the optimum response time. The thickness is preferably less than 0.5 mm. When preparing ion-sensitive field effect transistors (ISFETS), thickness of from 2 to 10 $\mu m$, preferably from 3 to 7 $\mu m$ can be used.

The concentration of the polymeric ionic species in the membrane may vary from 0.1 to 0.00001 M, while the concentration of the ion to which the membrane is sensitive will be the same or greater.

The electrode body of the invention may have a variety of different forms. For example, the electrode may be a solid-state electrode such as a conductor or a semiconductor device, or a coated wire electrode. In a preferred embodiment of the invention, the sensor is an ion-sensitive field effect transistor or a coated wire electrode.

The electrochemical sensors of the invention are useful to determine the concentration of ionic species in solution. For example, they may be used to determine the concentration of halide ions such as chloride or bromide. They are particularly useful for determining the concentration of ionic surfactants in solution. Such surfactants may be anionic, e.g., alkyl sulphates or alkaryl sulphonates such as n-alkyl sulphates where the alkyl group contains from 8 to 10 carbon atoms and alkyl naphthalene sulphonates such as tri-isopropyl-naphthalene sulphonates. For this purpose, a cationic copolymer is used for the membrane. Alternatively, the surfactant may be cationic, e.g., cetyl trimethylammonium bromide, and the copolymer will have anionic groups.

Potential specific uses for the present sensors include the determination of free surfactant, by direct potentiometry, in water samples such as waste water from industrial or domestic applications. Total surfactant may be determined by potentiometric titration.

The present invention also provides a method of determining the concentration of an ionic species in an aqueous solution using an electrochemical sensor of the invention. In this method, the sensor is contacted with the solution to be tested and the ion concentration determined as a function of the potential of the electrode.

The invention is further illustrated with reference to the accompanying drawings. FIG. 1 shows in cross-section an ISFET device comprising a semiconductor substrate 10 made of silicon having a p-type doping polarity. Two separate diffusion regions 11 and 12 having an n-type doping polarity are located in the semiconductor substrate at the upper surface thereof. Diffusion region 12 is referred to as the source while diffusion region 11 is referred to as the drain. The diffusion regions are each about 1 or 2 $\mu m$ in depth, have a length of about 400 $\mu m$ and are spaced about 20 $\mu m$ apart. When the device is in use, a conducting channel 21 exists between the two diffusion regions. The channel is a lightly-doped n-type to provide a depletion mode device.

The surface of the semiconductor substrate 10 between the two diffusion regions is known as the gate. An electrically-insulating layer 13 of silicon dioxide covers the surface of the substrate 10 and is itself covered by a layer 14 of silicon nitride. The insulator material between the two diffusion regions is known as the gate insulator.

Aluminum layers 15 and 16 are deposited on the source diffusion region 11 and the drain diffusion region 12, respectively, to provide electrical contacts therewith.

An ion-sensitive polymer membrane 17 is deposited over the insulating layers 13 and 14 above the gate region of the device. A layer 18 comprising an epoxy resin and polyimide mixture covers the electrical contacts to the source and the drain to shield them from a solution to be analyzed.

FIG. 1 shows the ISFET in use. The ion-sensitive membrane 17 is in contact with a solution 19 to be analyzed which contains ions to which the membrane 17 is sensitive. A reference electrode 20 coupled to a voltage source is provided in the solution. A voltage source is also provided between the source diffusion region 11 and the drain diffusion region 12 to establish a potential difference sufficient to cause current flow in the conducting channel 21 between the diffusion regions 11, 12.

Ions in the solution 19 interact with the ion-sensitive membrane 17 to produce a potential difference between the solution 19 and the membrane 17, thereby creating an electric field in the conducting channel 21. The strength of the electric field depends on the concentration of ions in solution 19 and controls the magnitude of the current flowing through the conducting channel 21, i.e., the drain current.

In order to determine the response of the ISFET to various concentrations of ions using the scheme illustrated in FIG. 1, the drain current is set by applying a constant voltage, e.g., 12 volts to a variable resistor 22, e.g., 120k ohm, and held constant by the operational amplifier 23 while the concentration of ions in solution is varied. The operational amplifier 23, working in inversion, is used to apply a potential to the gate of the device via the reference electrode 20 and the solution 19 such that electrochemically induced potential changes are offset. The potential applied in order to offset the electrochemically induced voltage changes, and thus maintain the drain current, varies in accordance with the concentration of ions in solution and a plot of reference electrode potential against ion concentration provides a calibration curve for the ISFET.

The following Examples are included for a better understanding of the invention.

Preparation 1—Preparation of poly(methyl methacrylate-co-1-vinylimidazole)

The polymerization of methyl methacrylate (44 g) and 1-vinylimidazole (9.4 g) in the presence of azobisisobutyronitrile (0.055 g) was performed in bulk monomer, under a nitrogen blanket, in a 0.1 l. flask fitted with a condenser. The contents of the flask were stirred continuously throughout the two hour duration of the reaction, the temperature being maintained at 60° C. by immersion in an oil bath. The copolymer was recovered by precipitation into an excess of diethyl ether, filtered and reprecipitated before final filtration and drying overnight in a vacuum oven at ambient temperature. An off-white, brittle polymer was obtained which was easily pulverized to a fine powder.

The elemental analysis of the product was as follows: C, 57.2; H, 7.7; N, 4.1%. This corresponds to a methyl methacrylate: 1-vinylimidazole ratio of 5.92:1.

Preparation 2—Quaternization of poly(methyl methacrylate-co-1-vinylimidazole)

A 0.5 l flask, fitted with a condenser and a nitrogen inlet and immersed in an oil bath maintained at 100° C. was charged with poly(methyl methacrylate-co-1-vinylimidazole) (7.4 g) and dioxan (200 g) and the contents were stirred. When the polymer had dissolved, benzylchloride (3.7 g; approximately 5-fold in excess) was added. The reaction mixture was allowed to reflux, with continuous stirring and nitrogen purging, for 20 hours. The product was recovered as in Example 1. Once again, the off-white product was easily pulverized to a fine powder.

The elemental analysis of the product was as follows: C, 58.0; H, 8.0; N, 1.6; Cl, 2.9%. This corresponds to a methyl methacrylate: 1-vinylimidazole (quaternized) ratio of 14.82:1. The $T_g$ of the quaternized copolymer was 113° C.

Preparation 3—Exchange of dodecyl sulphate anion for chloride counteranion of quaternized poly(methyl methacrylate-co-1-viylimidazole)

The quaterized copolymer of Example 2 (0.8 g) was dissolved in methanol and the resultant solution was added dropwise to a solution of sodium dodecyl sulphate (0.3 mol/l; 50 ml). The white precipitate that formed was filtered off, washed with water, and dried in an oven at 60° C. for 24 hours.

EXAMPLE 1

Surfactant-sensitive coated wire electrode

The copolymer of Preparation 3 (0.46 g) and a plasticizer, tricresyl phosphate (0.23 g), were dissolved in the minimum amount of tetrahydrofuran required for dissolution to form a very pale brown transparent solution.

About 2.5 cm of the outer insulation was removed from the end of a length of coaxial cable. The inner copper core (0.9 mm diameter) so exposed was coated with the copolymer/plasticizer solution to form a membrane having a thickness less than 0.5 mm. The outer screen of the cable was protected by the use of heat-shrinkable tubing.

Figure 3:
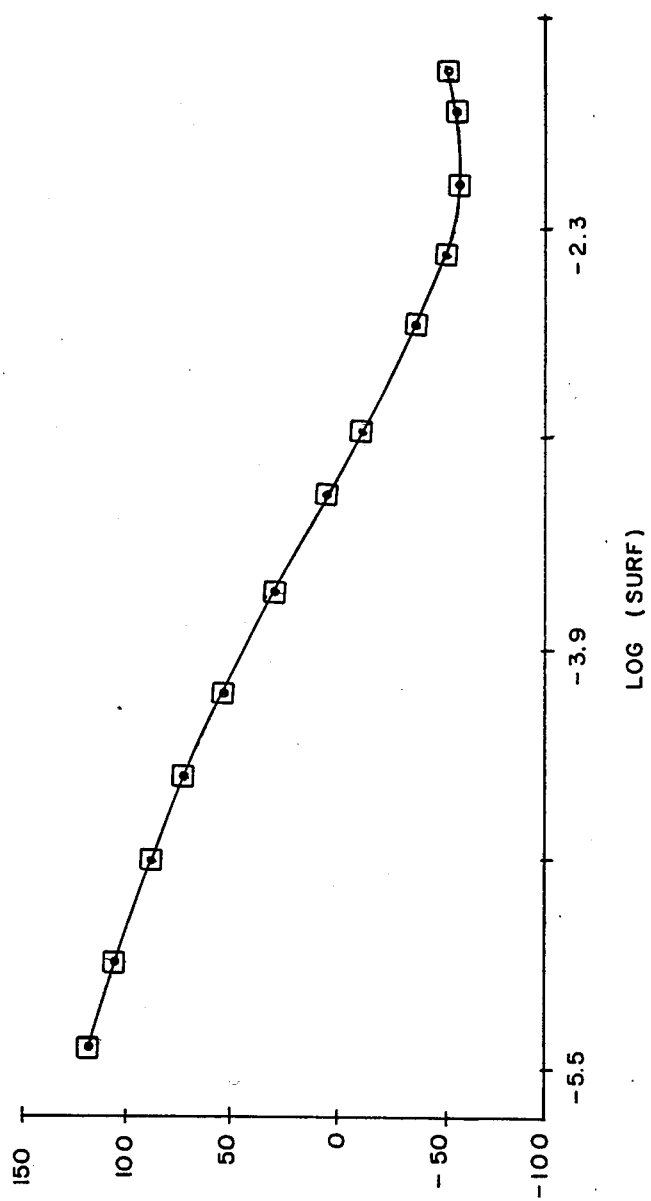
FIG. 3 is a graph showing the response of a coated wire electrode in accordance with the invention at various concentrations of the chloride.

The response characteristics of the surfactant sensitive coated wire electrode were as follows:
linear range 0.000022–0.00416 mol/l
slope 60.5 mV/decade
limit of detection 0.0000044 mol/l The equilibrium response time of less than 30 seconds was comparable with those of more conventional (liquid ion exchange) surfactant sensors. A calibration curve for the coated wire electrode is given in FIG. 3, which plots the response of the electrode (in mV) at various dodecyl sulphate concentrations (in mol). A double junction electrode was used as reference. The measurements were carried out at room temperature.

EXAMPLE 2

Chloride sensitive coated wire electrode

A coated wire electrode was prepared in the same manner as in Example 1 except that the copolymer of Preparation 2 was used instead of the copolymer of Preparation 3.

Figure 4:
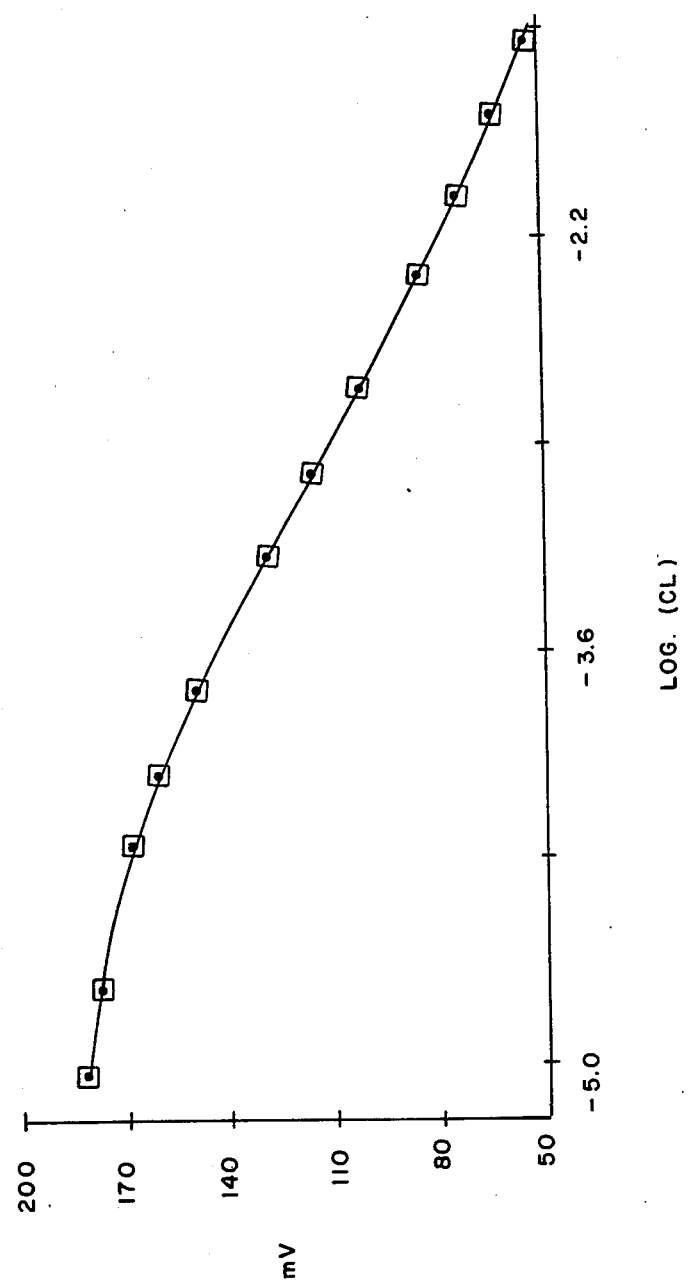
FIG. 4 is a graph showing the response of a coated wire electrode in accordance with the invention at various concentrations of chloride.

The response of the electrode prepared to chloride is given in FIG. 4 of the accompanying drawings, which plots the response of the electrode (in mV) at various chloride concentrations (in mol). A potassium chloride solution was used as the source of chloride ions. A double junction electrode was used as reference. The measurements were carried out at room temperature.

EXAMPLE 3

Chloride sensitive coated wire electrode

A coated wire electrode was prepared in the same manner as in Example 1 except that a copolymer of methyl methacrylate and 4-vinylpyridine quaternized with benzyl chloride was used. The molar ratio of methyl methacrylate to 4-vinylpyridine was 9.6:1 and the $T_g$ of the copolymer was 117° C.

The response characteristics of the chloride sensitive coated wire electrode were as follows:
linear range 0.000025–0.0091 mol/l
slope 39 mV/decade
limit of detection less than 0.000005 mol/l Measurements were carried out at room temperature using a potassium chloride solution as the source of chloride ions and a double junction reference electrode as the reference.

EXAMPLE 4

Surfactant sensitive ISFET

As ISFET of the type shown in FIG. 1 was employed wherein the ion-sensitive polymeric membrane was composed of the copolymer of Preparation 3 and had a thickness of about 5 μm.

Figure 2:
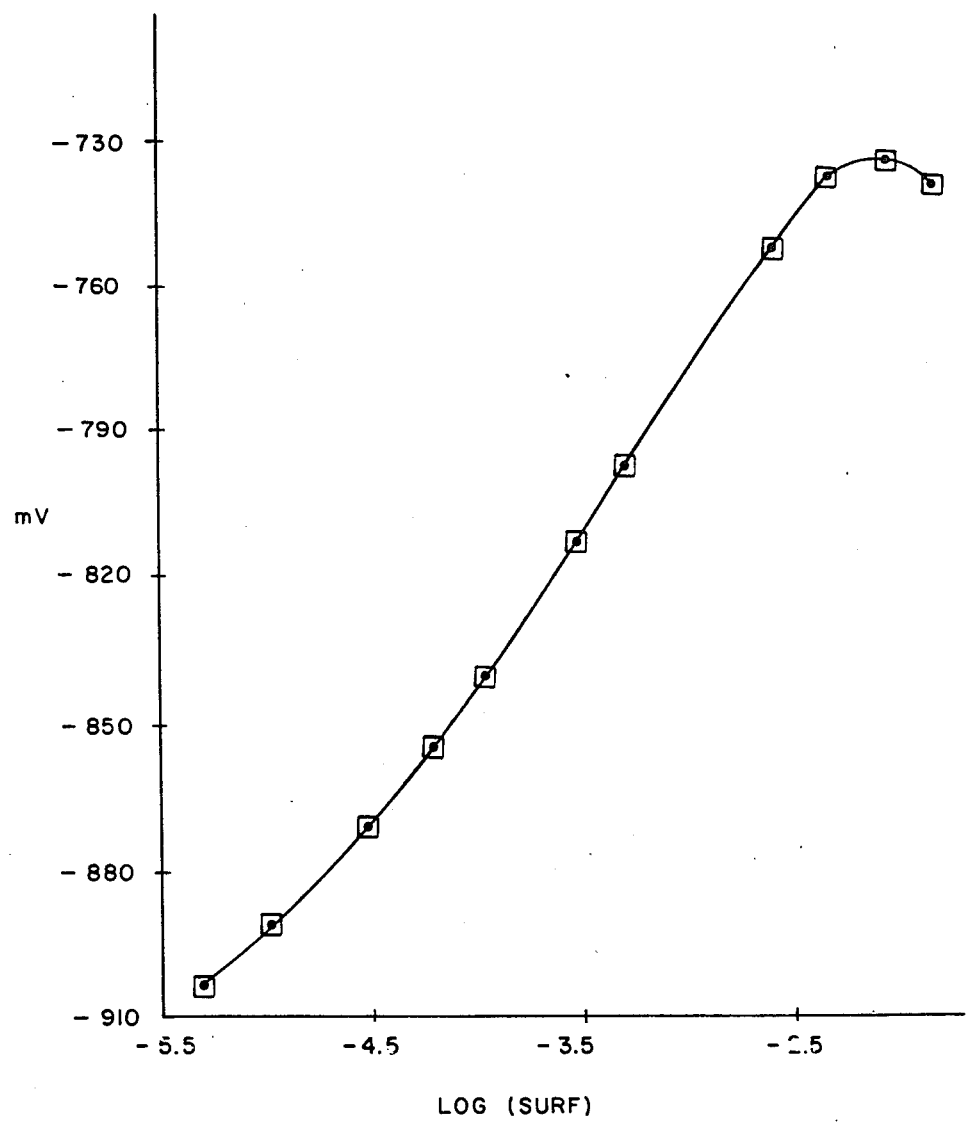
FIG. 2 is a graph showing the response of an ISFET in accordance with the invention at various concentrations of surfactant.

Using the method hereinbefore described with regard to FIG. 1, the response of the ISFET to dodecyl sulphate anion was measured. FIG. 2 plots the response of the ISFET (in mV) at various surfactant ion concentrations (in mol). Measurements were carried out at 25° C.

COMPARATIVE EXAMPLE

Poly(ethyl acrylate)$_{10}$-co-(1-vinyl-imidazole)$_1$ was prepared by a procedure identical to that of Example 1 of GB-A-No. 2 076 545. This polymer was then quaternized with benzyl chloride to give poly(ethyl acrylate)$_{10}$-co-(3-benzyl-1-vinylimidazolium chloride)$_1$ by a method identical to that of Example 2 of GB-A-No. 2 076 545. The poly(ethyl acrylate)$_{10}$-co-(3-benzyl-1-vinyl-imidazolium chloride)$_1$ was dissolved in methanol and coated to give a coated wire electrode in accordance with the procedure described in Example 1 of the GB-A No. 2 076 545. Because of the low $T_g$ of this polymer (<20° C.), no added plasticizer was necessary. The coated wire electrode did not function when titrated with a 1 molar sodium chloride solution, failing to come to equilibrium.

The invention has been described in detail with particular reference to preferred embodiments thereof, but it will be understood that variations and modifications can be effected within the spirit and scope of the invention.

We claim:

1. An ion-sensitive electrochemical sensor comprising an electrode body having an ion-sensitive polymeric membrane coated thereon, wherein the membrane comprises a water-insoluble copolymer having ion-exchange sites, said copolymer having a glass transition temperature greater than about 80° C.

2. A sensor according to claim 1 wherein the membrane further comprises a plasticizer.

3. A sensor according to claim 1 wherein the copolymer comprises from about 0.5 to 90% by weight of comonomer units having ion-exchange sites.

4. A sensor according to claim 3 wherein the copolymer comprises from about 5 to 25% by weight of comonomer units having ion-exchange sites.

5. A sensor according to claim 1 wherein the comonomer units having ion exchange sites contain quaternary ammonium groups.

6. A sensor according to claim 5 wherein the nitrogen atoms of the quaternary ammonium groups form part of a heterocyclic ring.

7. A sensor according to claim 6 wherein the comonomer units having ion-exchange sites are derived from vinylimidiazole and vinylpyridine.

8. A sensor according to claim 1 wherein the copolymer contains comonomer units derived from methyl methacrylate.

9. A sensor according to claim 7 wherein the copolymer contains comonomer units derived from methyl methacrylate.

10. A sensor according to claim 1 that is sensitive to surfactant ions.

11. A sensor according to claim 1 that is sensitive to halide ions.

12. A method of determining the concentration of ions in an aqueous solution comprising the steps of:
    contacting the solution with an electrochemical sensor comprising an electrode body having an ion-sensitive polymeric membrane coated thereon, wherein the membrane comprises a water-insoluble copolymer having ion-exchange sites, said copolymer having a glass transition temperature greater than about 80° C., and
    determining the concentration of said ions in said solution as a function of the potential of the electrode.

* * * * *

UNITED STATES PATENT OFFICE
CERTIFICATE OF CORRECTION

PATENT NO. : 4,773,970
DATED : September 27, 1988
INVENTOR(S) : Purbrick et al.

It is certified that error appears in the above-identified patent and that said Letters Patent are hereby corrected as shown below:

Column 8, line 19

"vinylimidiazole"

sould read

--vinylimidazole--.

Signed and Sealed this

Twenty-first Day of February, 1989

Attest:

DONALD J. QUIGG

*Attesting Officer*     *Commissioner of Patents and Trademarks*